United States Patent [19]

Deal

[11] Patent Number: 5,401,252
[45] Date of Patent: Mar. 28, 1995

[54] SYRINGE SHIELD AND CAP HOLDING DEVICE

[76] Inventor: Richard E. Deal, 614 S. Moore, Algona, Iowa 50306

[21] Appl. No.: 222,489

[22] Filed: Apr. 4, 1994

[51] Int. Cl.$^6$ .............................................. A61M 5/32
[52] U.S. Cl. ................................... 604/192; 604/263; 206/365
[58] Field of Search ....................... 604/192, 187, 263; 206/365

[56] References Cited

U.S. PATENT DOCUMENTS

| | | | |
|---|---|---|---|
| 86,016 | 1/1869 | Howell . | |
| 1,023,042 | 4/1912 | Scott . | |
| 2,977,150 | 3/1961 | Thomas | 294/118 |
| 4,596,562 | 6/1986 | Vernon | 604/263 |
| 4,717,386 | 1/1988 | Simmons | 604/192 |
| 4,742,910 | 5/1988 | Staebler | 206/365 |
| 4,795,443 | 1/1989 | Permenter et al. | 604/198 |
| 4,840,272 | 6/1989 | Goldman | 206/365 |
| 4,846,803 | 7/1989 | Emerson | 604/263 |
| 4,955,865 | 9/1990 | Steiner | 604/192 |
| 4,979,945 | 12/1990 | Wade et al. | 604/192 |
| 5,087,249 | 2/1992 | Deal | 604/192 |

FOREIGN PATENT DOCUMENTS

| | | |
|---|---|---|
| 103966 | 8/1926 | Austria . |
| 295888 | 12/1988 | European Pat. Off. . |
| 2620341 | 9/1987 | France . |
| 2202446 | 9/1988 | United Kingdom . |
| 2205043 | 11/1988 | United Kingdom . |
| WO8503006 | 1/1985 | WIPO . |
| WO8800477 | 6/1987 | WIPO . |
| WO8807873 | 4/1988 | WIPO . |

OTHER PUBLICATIONS

"Reduce the Risk of Needle Puncture Wounds", Comp-Gard, Easy to Use Effective Inexpensive, Comp Equipment Corporation, 3 sheets, Nov. 11, 1983.

Primary Examiner—John D. Yasko
Attorney, Agent, or Firm—Zarley, McKee, Thomte, Voorhees, & Sease

[57] ABSTRACT

A syringe shield and cap holding device is provided which allows a syringe cap to be safely removed and placed back on a syringe needle without exposing a user's hand or fingers to the needle. The device includes a handle and a cap receiving element which releasably secures the cap so that a user can remove and insert the syringe needle without danger of pricks or scratches. The cap receiving element is generally defined by a U-shaped member having a bottom leg, an intermediate curved web, and a top leg, with the legs frictionally engaging the syringe cap until a user laterally removes the cap from the cap receiving element. Rearward axial movement of the cap is prevented by a cap catch which engages the syringe cap when in the U-shaped member.

17 Claims, 5 Drawing Sheets

SYRINGE SHIELD AND CAP HOLDING DEVICE

BACKGROUND OF THE INVENTION

The present invention relates to a device for shielding a user of a syringe and for holding a syringe cap, and in particular, a device to enable the user of a syringe to remove the syringe cap and place the syringe cap on the syringe without exposing the user to the dangers associated with a contaminated syringe needle. The needle of a syringe is a hazard which medical personnel expose themselves to every day. Besides the painful pricks, scratches and cuts, medical personnel who handle syringes are subject to the possibility of contracting viruses and diseases, such as AIDS and hepatitis.

Generally, a syringe cap is placed over the needle to protect the needle from damage prior to use and to prevent injury to those who handle the syringe. In order to place the cap on the needle following use, users normally grasp the cap between their fingers and necessarily expose their fingers to the needle tip.

Therefore, a primary objective of the present invention is the provision of an improved syringe cap holder and shield.

Another objective of the present invention is the provision of a device for removing and holding a syringe cap and shielding a user, thereby allowing the user to place a syringe needle back within the cap safely.

Another objective of the present invention is tile provision of a syringe cap holder and shield which allows the user to remove the syringe cap and place a syringe cap on the syringe needle without exposing the user to the hazards of a needle prick.

A further objective of the present invention is the provision of a syringe cap holding device which allows a syringe cap to be removed from and placed onto a syringe without the user holding the cap.

Still another objective of the present invention is the provision of a disposable syringe cap holder and shield which is economical to manufacture, and safe and easy to use.

These and other objectives will become apparent from the following description of the invention.

SUMMARY OF THE INVENTION

A syringe shield and cap holding device is provided for safety and ease in removing a syringe cap from a syringe and replacing the cap onto the syringe. The device comprises a control member or handle which serves as a means for retaining the device in a fixed location, and a cap receiving member. The cap receiving member is adapted to receive the syringe cap and releasably secure that cap so a user can remove the syringe therefrom. The cap is then retained in position until the user places the syringe back inside the cap safely. A shielding member provides safety to a user by preventing his/her or hands or fingers from being scratched or pricked and is interposed between the control member and the cap receiving means.

The device may take several alternative shapes. For example, the control member may be shaped so as to rest upon a table. Further, the device may be shaped so as to be integrated in a pan or medicine dispensing tray. Finally, the device may be clipped or attached to a pole or post.

In use, the capped syringe is inserted into the cap receiving means which firmly grips or holds the cap, such that the syringe can be removed from the cap without the user holding the cap. The cap is secured in the cap receiving means until the user selects to place the syringe needle back within the cap. After placing the syringe back in the cap, the entire syringe, with the cap covering and protecting the needle, can be removed from the syringe shield and cap holding device by laterally sliding the cap out of the cap receiving member. Since the user's hand and fingers are located away from the syringe cap and shielded from the syringe at all times, the user can avoid an accidental needle prick, thereby eliminating the hazards associated with handling a syringe.

DESCRIPTION OF THE PREFERRED EMBODIMENT

Figure 1:
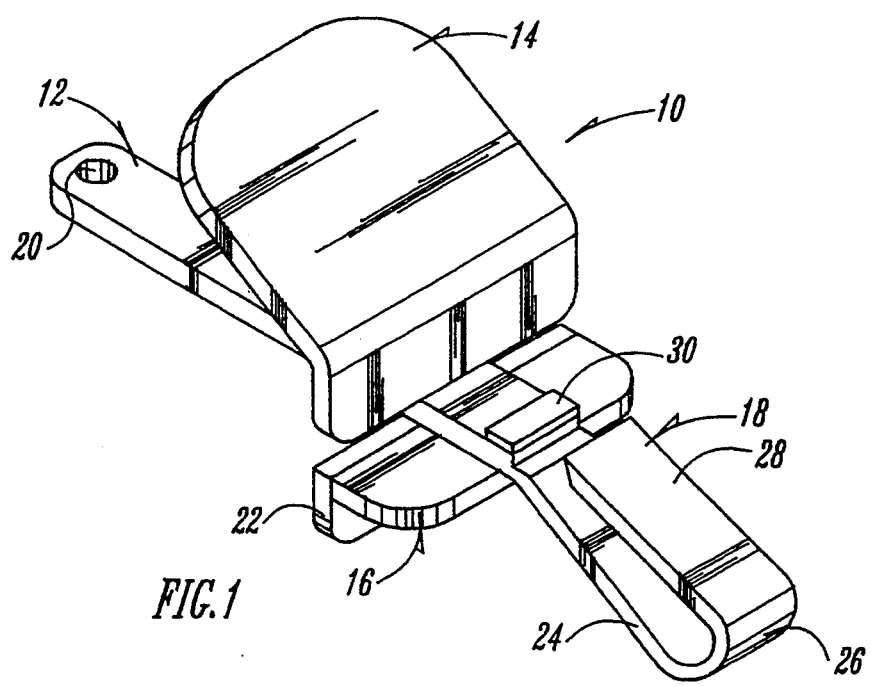
FIG. 1 is a perspective view of the syringe shield and cap holding device of the present invention.
Figure 2:
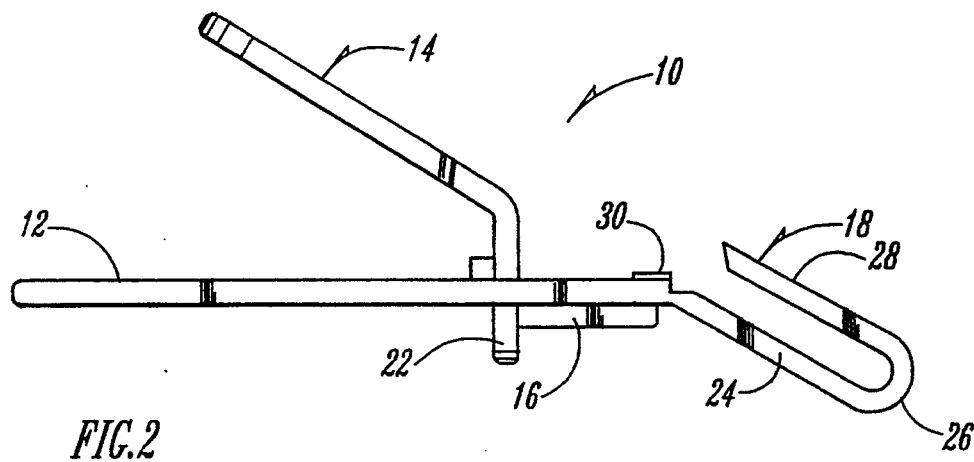
FIG. 2 is a side elevational view of the device shown in FIG. 1.
Figure 3:
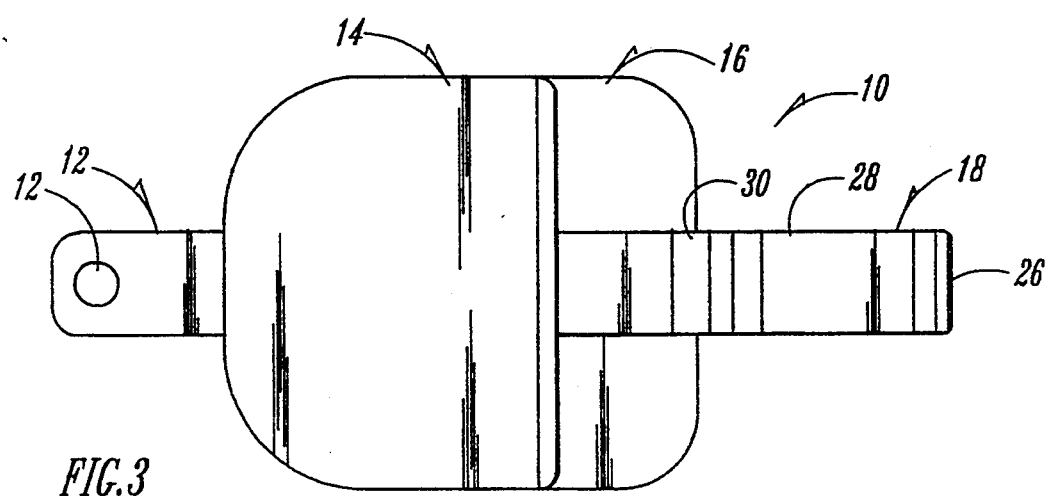
FIG. 3 is an overhead plan view of the device shown in FIG. 1.
Figure 4:
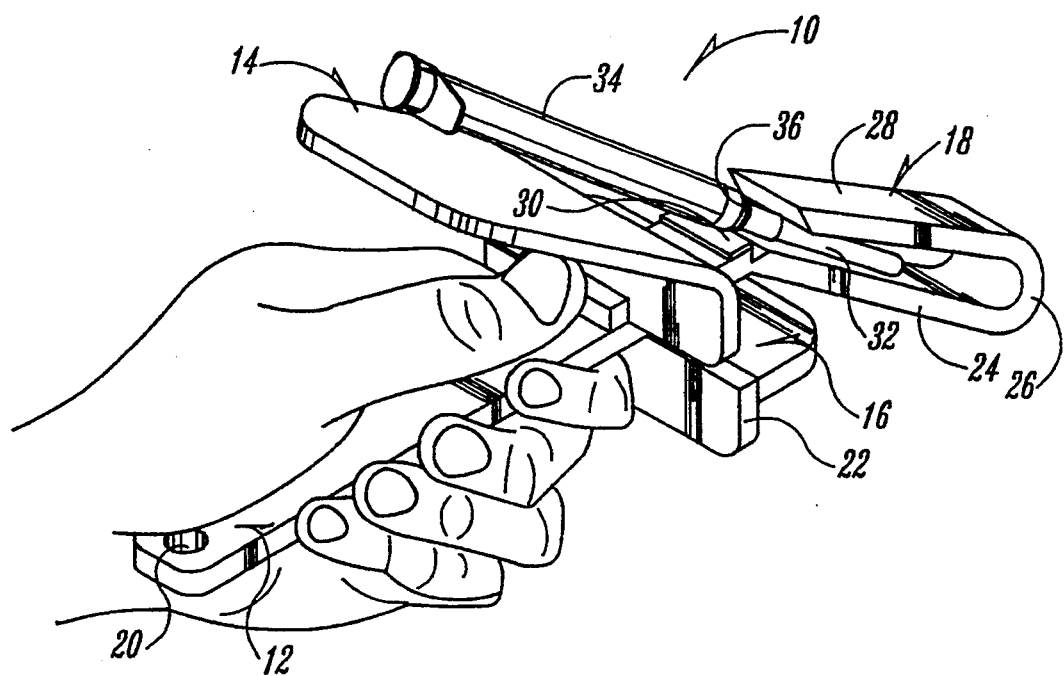
FIG. 4 is a perspective view of the device being used in conjunction with a syringe and syringe cap.

Referring to the drawings, the syringe shield and cap holding device is generally designated by the reference numeral 10. The device 10 is comprised of a control member or handle 12, an upper shield member 14, a lower shield member 16, and a generally U-shaped cap receiving element 18. The shield members 14 and 16 are positioned between the handle 12 and cap receiving element 18, with the handle and cap receiving element extending in opposite directions from the shield members.

The handle 12 is substantially rectangular and has an aperture 20 provided so the syringe shield and cap holding device 10 can be hung in a convenient location. The upper shield member 14 is substantially wider than the handle 12 and is generally positioned between the handle 12 and the cap receiving element 18. The upper shield member 14 extends generally upwardly from the handle 12 and extends away from the cap receiving element 18 and over the handle 12 so as to provide protection to a user's hand and fingers. The lower shield member 16 of this embodiment is coplanar or parallel to the handle 12 and extends the protection of the syringe shield and cap holding device 10. A stabilizing element 22 is also provided so that when the device 10 is positioned on a flat or planer surface, such as a table, it remains stable and has three point contact with the surface. This contact occurs at the handle 12, the stabilizing element 22 and the distal curved end 26 of the cap receiving element 18.

The cap receiving element 18 is generally U-shaped. The element 18 is comprised of a bottom leg or wall 24, an intermediate curved web or wall 26, and an upper wall 28. The walls 24, 26 and 28 define a channel between the walls with an open rearward or upper end and a closed forward or lower end. The bottom wall 24 extends from the handle 12 at a non-parallel and obtuse angle.

Figure 5:
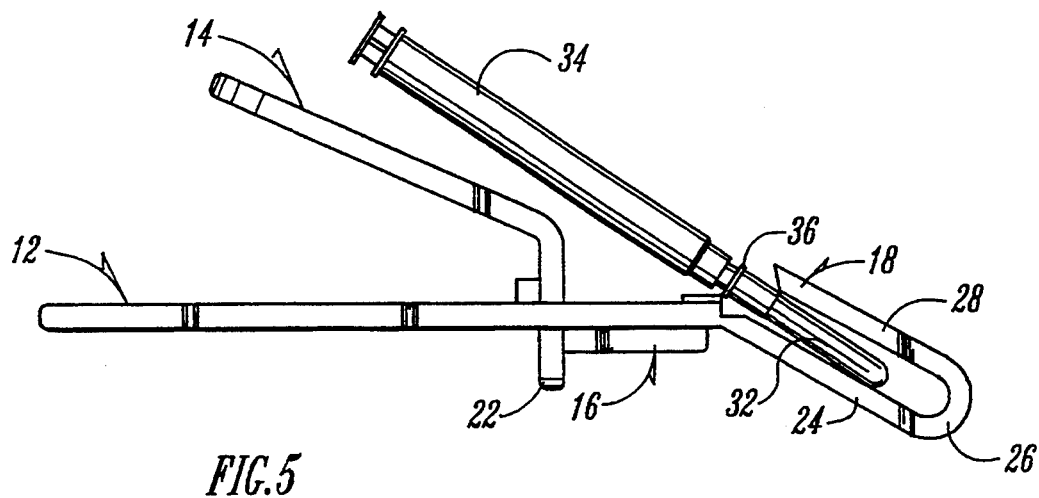
FIG. 5 is a side elevational view of the device shown in FIG. 4.

A cap catch 30 is located at the juncture of the handle 12 and the bottom wall 24. The U-shaped cap receiving element 18 is elongated so as to receive and securely hold a syringe cap 32 when the cap 32 is inserted past the catch 30, as seen in FIG. 5. The catch 30 engages the open end of the cap to prevent rearward axial movement of the cap, thereby allowing the syringe 34 to be withdrawn from the cap 32.

As shown more closely in FIG. 5, the syringe 34 is positioned in the syringe shield and cap holding device 10 by inserting the syringe cap 32 axially into the channel between the bottom wall 24, the upper wall 28 of the cap receiving element 18. The syringe cap 32 is pushed into the cap receiving element 18 so that the lip 36 of the syringe cap 32 is positioned on the side of the catch 30 opposite the handle 12. The syringe cap 32 is secured and further axial movement is prevented by catch 30 and pressure from the cap receiving element 18. The bottom wall 24 and upper wall 28 frictionally engage the syringe cap 32 when the syringe cap 32 is positioned therebetween so as to allow the syringe 32 to be removed from the cap 32, by pulling the syringe 34 axially away from the secured syringe cap 32.

When the user is through with the syringe 34, the syringe 34 is inserted back into the securely positioned syringe cap 32. The syringe cap 32 and syringe 34 can be laterally turned or slid out of the side opening of the cap receiving member 18. By using the device 10, the user's hand and fingers are remote from the cap 32 while the syringe 34 is removed from and inserted into the cap 32. As a result, the user is less likely to be pricked or scratched by the needle.

Alternative embodiments of the device 10 are shown in FIGS. 6-14. Structure similar to that described above with respect to device 10 is designated with the same reference numeral in FIGS. 6-8, with the suffixes "A", "B", "C", "D", or "E" added.

Figure 6:
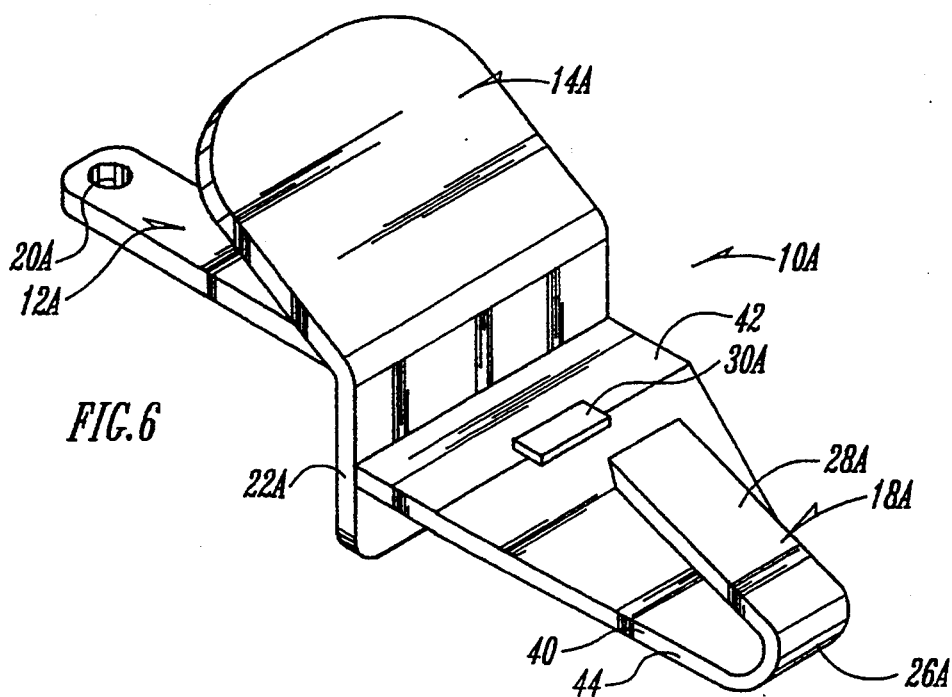
FIG. 6 is a perspective view showing an alternative embodiment shielding member having an extended shielding means for greater protection.
Figure 7:
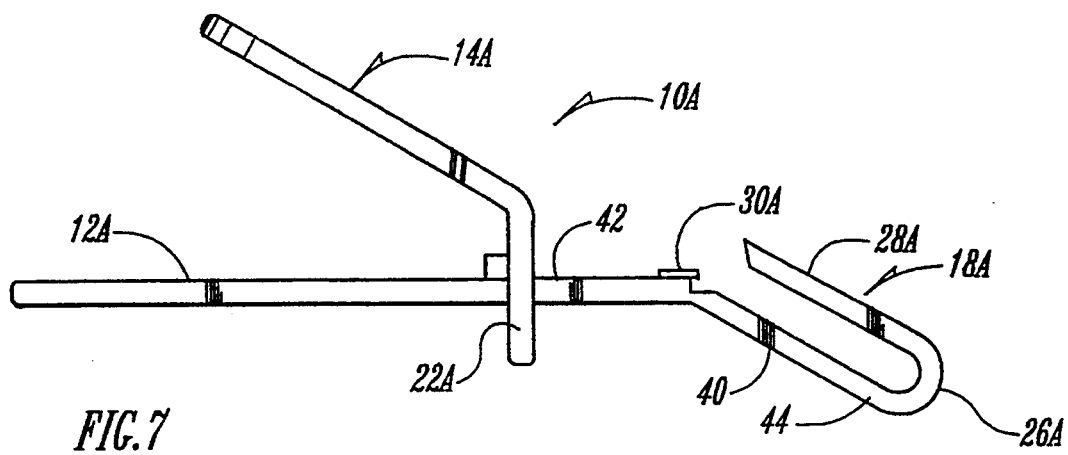
FIG. 7 is a side elevational view of the device shown in FIG. 6.
Figure 8:
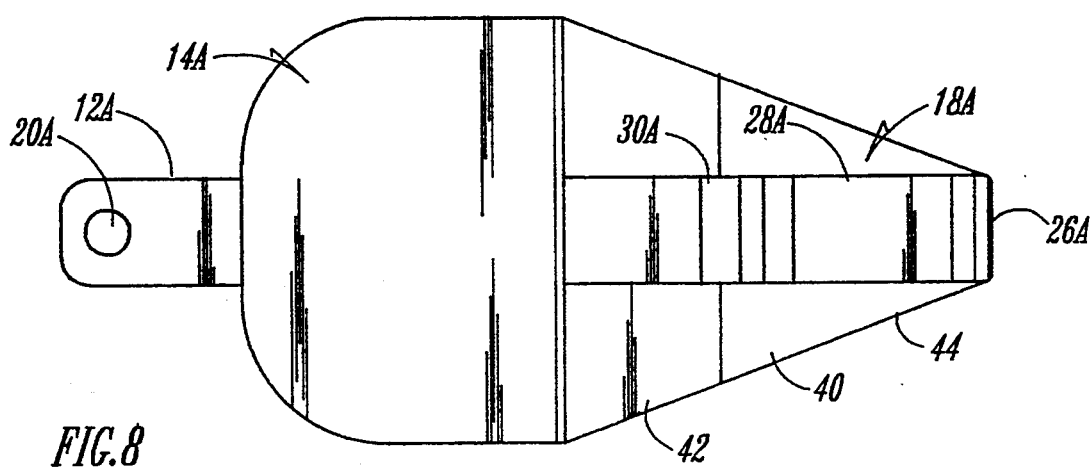
FIG. 8 is an overhead plan view of the device shown in FIG. 6.

An alternative embodiment 10A of the syringe shield and cap holding device is shown in FIG. 6 through 8. The syringe shield and cap holding device 10A has a handle 12A, an upper shield member 14A, and a stabilizing element 22A. The lower shield member 16 and the bottom wall 24 of the prior embodiment 10 are integrated into a single bottom shield 40 comprised of a first shield wall portion 42 and an angled bottom wall portion 44. The intermediate curved wall 26A and upper wall 28A are integral with portion 44 so as to form the cap receiving element 18A. This embodiment extends the shielding benefits of the previously described embodiment.

Figure 9:
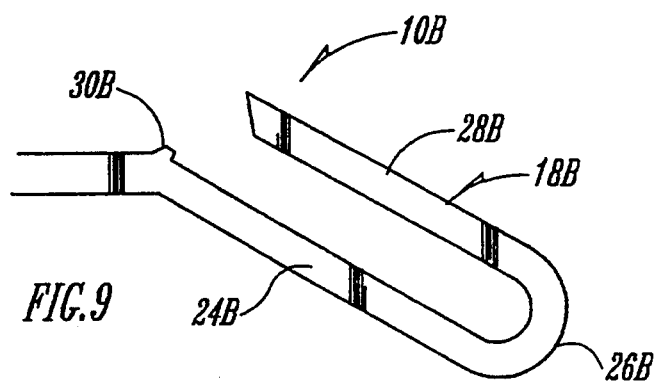
FIG. 9 is a side elevational view of another alternative embodiment of the catch on the cap receiving member.
Figure 10:
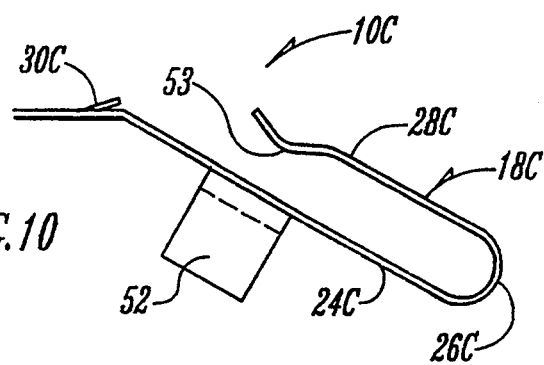
FIG. 10 is a side elevational view of the cap receiving of an alternate embodiment mounted on a pole.
Figure 11:
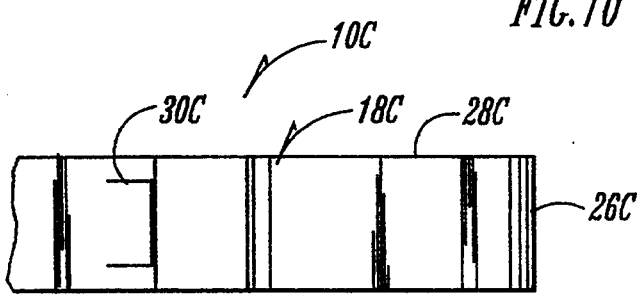
FIG. 11 is an overhead plan view of the device of FIG. 10.

The syringe shield and cap holding devices 10 and 10A are formed generally of a molded polymeric material, but other materials are anticipated and the device should not be limited to any one substance. For example, in the first embodiment, the catch 30 is attached as a separate piece to the device 10. FIG. 9 shows an alternative embodiment wherein the cap receiving element 18B and catch 30B can be molded out of a polymeric material into a one-piece unit. FIG. 10 shows a further embodiment wherein the device 10C is formed from a curved metal strip, with the catch 30C punched from the metal strip. A clip 52 is provided on leg 24C to secure the device to a post or IV pole. The upper leg 28C includes a curved portion 53 for exerting pressure on the cap.

Figure 12:
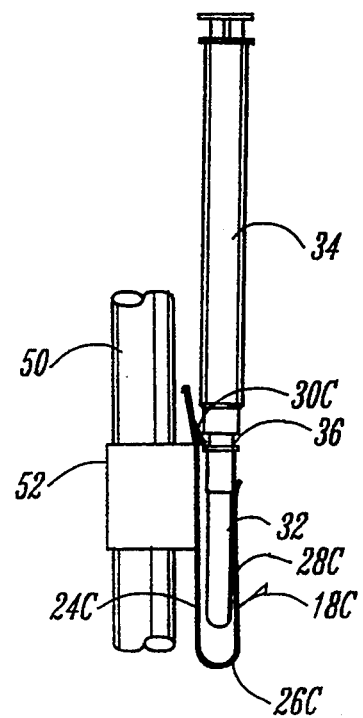
FIG. 12 is a side elevational view of the device of FIG. 10 shown attached to a cylindrical or tubular body.

FIG. 12 shows another embodiment wherein the cap receiving element 18C can be mounted on a post or bed frame 50 through the use of a C-shaped clip 52, or other securement means. The post 50 serves as both a shield and a control member retaining the stability of the element 18C, while maintaining the advantage of keeping a user's hand and fingers from the syringe 34 when it is removed from and placed back in the syringe cap 32.

Figure 13:
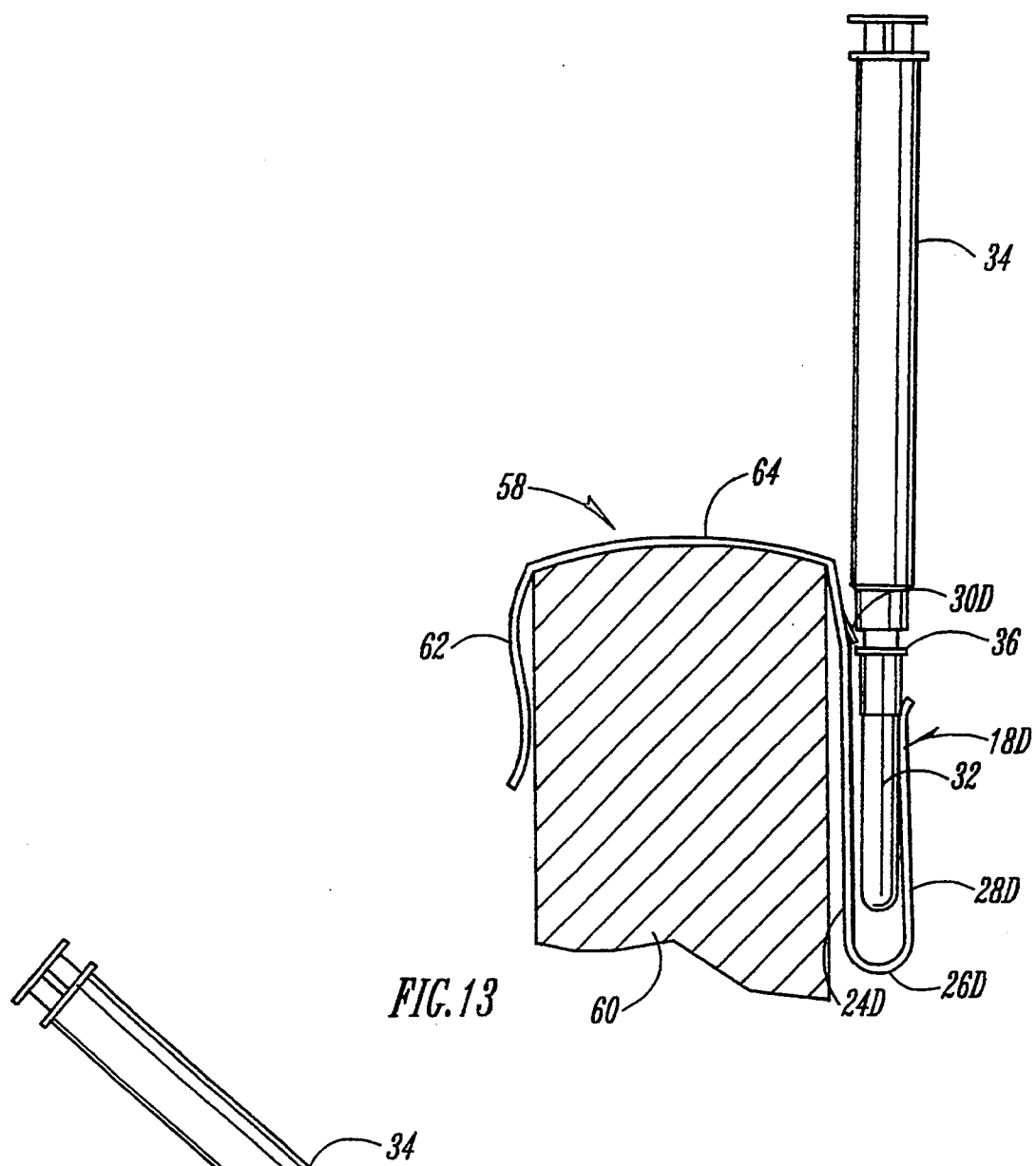
FIG. 13 is a side elevational view of the device of an alternative embodiment shown clipped to the top of a bed frame.

FIG. 13 shows another alternative embodiment wherein the cap receiving element 18D is connected to a control member or hook 58 which forms a clip that can be attached to the top of a bed or post 60 and can be removably secured thereon. The clip 58 is comprised of a top portion 62 and a flexible biased portion 64 which put pressure on the post 60 to hold the device 10 in place.

Figure 14:
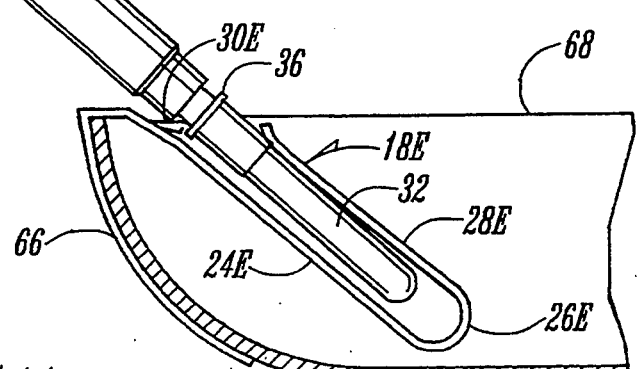
FIG. 14 is a side partial sectional view showing an alternative embodiment of the device mounted within a tray or pan.

FIG. 14 shows a final alternative embodiment wherein the device includes a control member or hook 66 which is adapted to be releasably secured on the side of a tray or bowl 68.

It is understood that the handle/control means of the device can be modified so as to have any shape which is comfortable to the user or which can be attached to various surfaces, equipment, or structures, especially those found in a hospital environment. Further modifications, such as the provision of finger grooves in the handle, are anticipated. Also, the angle between the handle and the cap receiving element may vary, depending on the shape of the handle or control member and other design considerations.

It is understood that modifications can be made to the syringe shield and cap holding device described above without departing from the scope of the present invention. In the drawings and specification there has been set forth a preferred embodiment of the invention, and although specific terms are employed, these are used in a generic and descriptive sense only, and not for the purposes of limitation. Changes in the form and the proportion of parts as well as in the substitution of equivalents are contemplated as circumstances may suggest or render expedient without departing from the spirit or scope of the invention as defined in the following claims.

What is claimed is:

1. A syringe cap holding device, comprising:
   a handle;
   a cap holding member connected to the handle for releasably retaining a syringe cap, the cap holding member being adapted to receive and hold the syringe cap while a user removes a syringe from the cap and while the user replaces the syringe into the cap; and a shield positioned between the handle and the cap holding member, such that the handle and cap holding member extend in opposite directions from the shield.

2. The device of claim 1 wherein said cap holding member comprises:

a generally U-shaped portion extending from the handle; and a syringe cap catch adapted to engage the syringe cap when the user pulls the syringe from the cap after securing the cap in the cap holding member so as to prevent axial movement of the cap.

3. The device of claim 2 further comprising attachment means for securing the device to a support member.

4. The device of claim 3 wherein the attachment means comprises an aperture in the handle for hanging the device from a hook.

5. The device of claim 3 wherein the attachment means comprises a strap for attaching the device to a post.

6. The device of claim 3 wherein the attachment means comprises a hook for hanging the device on a support member.

7. The device of claim 2 wherein the U-shaped portion has an open upper end adapted to axially receive a syringe cap.

8. The device of claim 2 further comprising a stabilizing arm.

9. A syringe cap holding device, comprising:

a U-shaped member having a first leg, a second leg, and a web interconnecting the first and second legs to form an elongated channel having a closed forward end and an open rearward end between the first and second legs, the member being adapted to axially receive a syringe having a syringe cap into the open upper end whereby the first and second legs frictionally engage and retain the cap while the syringe is removed from the cap; and a cap catch extending from one of the legs adjacent the rearward end of the channel to prevent the cap from moving axially rearwardly when the syringe is removed from the cap.

10. The device of claim 9 further comprising a clip on one of the legs for securing the device to a support member.

11. The device of claim 9 further comprising a handle extending rearwardly from one of the legs.

12. The device of claim 11 further comprising a shield positioned between the U-shaped member and the handle.

13. The device of claim 9 further comprising a strap attached to one of the legs to secure the U-shaped member to a support member.

14. A syringe cap holding device, comprising:

a U-shaped member having a first leg, a second leg, and a web interconnecting the first and second legs to form an elongated channel having a closed forward end and an open rearward end between the first and second legs, the member being adapted to axially receive a syringe having a syringe cap into the open upper end whereby the first and second legs frictionally engage and retain the cap while the syringe is removed from the cap;

a handle extending rearwardly from one of the legs; and a shield positioned between the U-shaped member and the handle.

15. The device of claim 14 further comprising a cap catch extending from one of the legs adjacent the rearward end of the channel to prevent the cap from moving axially rearwardly when the syringe is removed from the cap.

16. The device of claim 14 further comprising a clip on one of the legs for securing the device to a support member.

17. The device of claim 14 further comprising a strap attached to one of the legs to secure the U-shaped member to a support member.

* * * * *